(12) United States Patent
Von Krosigk et al.

(10) Patent No.: US 7,267,888 B1
(45) Date of Patent: *Sep. 11, 2007

(54) PRODUCTS CONTAINING AN ANTI-FUNGAL AMOUNT OF A SALT OF FORMIC ACID

(76) Inventors: James Richard Von Krosigk, 2625 Cowey Rd., Nixon, TX (US) 78140; Thomas E. Peterson, 1143 Rennie Dr., Katy, TX (US) 77450

( * ) Notice: Subject to any disclaimer, the term of this patent is extended or adjusted under 35 U.S.C. 154(b) by 36 days.

This patent is subject to a terminal disclaimer.

(21) Appl. No.: 10/965,051

(22) Filed: Oct. 14, 2004

Related U.S. Application Data

(63) Continuation of application No. 10/408,802, filed on Apr. 7, 2003, now Pat. No. 6,821,637.

(51) Int. Cl.
*B32B 9/00* (2006.01)

(52) U.S. Cl. .............. 428/537.5; 428/537.7; 428/688; 428/703; 106/15.05; 106/18.36; 106/772; 442/123; 442/412

(58) Field of Classification Search .......... 428/537.5, 428/537.7, 688, 703; 106/15.05, 18.36, 772; 442/123, 412
See application file for complete search history.

(56) References Cited

U.S. PATENT DOCUMENTS

| | | | | |
|---|---|---|---|---|
| 2,976,183 A * | 3/1961 | Arthur | ............... | 8/196 |
| 4,335,109 A | 6/1982 | Hill | ............... | 424/140 |
| 5,106,407 A | 4/1992 | Relenyi | ............... | 71/88 |
| 6,060,086 A | 5/2000 | Belanus | ............... | 424/686 |
| 6,726,936 B1 | 4/2004 | Asano | ............... | 424/618 |
| 2002/0187169 A1 | 12/2002 | Chen | ............... | 424/401 |
| 2003/0060504 A1 * | 3/2003 | Yoshida et al. | ............... | 514/460 |

OTHER PUBLICATIONS

The Merck Index; Encyclopedia; 1983; pp. 551, 870, and 1456; Tenth edition; Merck and Co., Inc.; Rahway, NJ USA.
Erich Lueck; Antimicrobial Food Additives; Section 22 Acetic Actid.

* cited by examiner

*Primary Examiner*—Andrew Piziali
*Assistant Examiner*—Peter Y Choi
(74) *Attorney, Agent, or Firm*—Buskop Law Group, PC; Wendy Buskop

(57) ABSTRACT

A building material adapted for controlling growth of vegetative fungi from spores having a compressed calcium sulfate layer, a paper layer over the sulfate layer, an adhesive for securing the paper layer to the sulfate layer; an amount of between about 30 wt % to 50 wt % of a salt of formic acid disposed on the paper layer thereby forming sheet rock with an ionic lattice on the surface to prevent vegetative growth from fungi spores, and a paint, an adhesive, a sealant, and an insulation each containing an antifungal amount of a salt of formic acid, such as potassium formate.

36 Claims, No Drawings

PRODUCTS CONTAINING AN ANTI-FUNGAL AMOUNT OF A SALT OF FORMIC ACID

The present application is a continuation of U.S. application Ser. No. 10/408,802 filed on Apr. 7, 2003, now U.S. Pat. No. 6,821,637, and titled "PRODUCTS CONTAINING AN ANTIFUNGAL AMOUNT OF A SALT OF FORMIC ACID".

FIELD OF THE INVENTION

The present invention relates to products containing an anti-fungal amount of a salt of formic acid.

BACKGROUND OF THE INVENTION

The present invention relates to products containing an anti-fungal amount of a salt of formic acid. The invention was designed to control the growth by killing the vegetative fungi or mold germinating from spores of the fungi with an additive that can be blended into commercially available paints, spackle, adhesives, grout, and sealants used in the home and commercial construction industry. The additive can also be used in the paper making industry to control growth of spores during the making of paper that causes spoilage. The additive can also be used to control the growth of bacterial in automotive and air conditioning end uses by adding it to lubrication systems of cars, compressors for oil field drilling, transmission systems or cars and other motors, air conditioning and heating systems and the like.

An object of the invention is to provide an easy to use, environmentally friendly additive which is cheaper than those currently commercially available.

Another object of the invention is to provide an additive that is light and easy to transport additive.

A final object of the invention is to provide and additive that does not cake or clog and can be easily flowed into a system in a continuous flow without the need to batch addition of the additive.

SUMMARY OF THE INVENTION

The invention relates to a building material adapted for controlling growth of vegetative fungi from spores comprising: a compressed calcium sulfate layer, a paper layer over the sulfate layer, an adhesive for securing the paper layer to the sulfate layer; an amount of between about 30 wt % to about 50 wt % of a salt of formic acid disposed on the paper layer thereby forming sheet rock with an ionic lattice on the surface to prevent vegetative growth from fungi spores, and a paint, an adhesives, a sealant, and an insulation each containing an antifungal amount of a salt of formic acid, such as potassium formate.

The invention relates to products containing a formulation which is contemplated to kill the spores of fungus which includes in particular certain *penicillium* species and certain *Stachybotrys* species

DETAILED DESCRIPTION

Before explaining the present invention in detail, it is to be understood that the invention is not limited to the particular embodiments and that it can be practiced or carried out in various ways.

Biological fouling due to the growth of spores after pretreatment to control the fungi is a serious economic problem in many commercial and industrial uses.

The growth of fungi or mold from spores has wreaked havoc in the home insurance industry, where families have to be moved out of their homes to treat the initial killing of the fungi growth, only to discover a year or two later that the fungi has grown back creating a serious health hazard.

Fungi known as *strachybotrys* species, *penicillium* species and various *aspergillus* species create spores to propagate. Although numerous commercial additives exist to kill the vegetative growth of the fungi, typically these additives must be used in extremely high and toxic concentrations to destroy the spores of these fungi. The use of high concentrations of these known additives, when added to aqueous systems, destroys valuable intrinsic properties of the formulation to which they are added. For example, if bleach is used to kill vegetative fungus, and it is added in high concentration to a condensation system of an air conditioner, typically, the polar characteristics of the lubricant fluid would be harmed. Also, other additives, when added in quantities large enough to additionally kill fungi from the spores, have resulted in clogged system, without the continued ability to flow freely.

A need has existed for various products with an additive applied which does not destroy the underlying advantages of the aqueous system to which it is added which may include the fundamental chemical characteristics of that system.

The present invention addresses these needs.

The various embodiments of this invention relate to a building material adapted for controlling growth of vegetative fungi from spores having, a compressed calcium sulfate layer, a paper layer over the sulfate layer, an adhesive for securing the paper layer to the sulfate layer, 30 wt % to 50 wt % of an amount of a salt of formic acid disposed on the paper layer thereby forming sheet rock with an ionic lattice on the surface to prevent vegetative growth from fungi spores, and a paint, an adhesives, a sealant, and an insulation each containing an antifungal amount of a salt of formic acid, such as potassium formate.

The invention relates to products containing a formulation which is contemplated to kill the spores of fungus which includes in particular certain *penicillium* species and certain *stachybotrys* species.

The salt of formic acid is potassium formate. Further, a second salt of formic acid can be added to the materials. The building materials can also include a salt of citric acid, oxalic acid, maleic acid, acetic acid, fumaric acid, humic acid, fulvic acid, malic acid, glutaric acid, or glutamic acid.

In an alternate embodiment, the building materials can include an encapsulation agent to encapsulate the spores. The preferred encapsulation agent is colloidal oatmeal.

An embodiment of the invention can be a paint comprising between about 30 wt % to about 50 wt % of a salt of formic acid capable of forming an ionic lattice on a surface to which paint is applied to prevent vegetative growth from fungi spores.

An embodiment of the invention is also contemplates an adhesive comprising from about 30 wt % to about 50 wt % of a salt of formic acid capable of forming an ionic lattice on a surface to which adhesive is applied to prevent vegetative growth from fungi spores.

An embodiment of the invention is also an insulation comprising from about 30 wt % to about 50 wt % of a salt of formic acid disposed on the surface of the insulation adapted to form an ionic lattice on the surface thereby preventing vegetative growth from fungi spores.

An embodiment of the invention is also a sealant comprising from about 30 wt % to about 50 wt % of a salt of formic acid which forms an ionic lattice on the surface to which the adhesive is formed to prevent vegetative growth from fungi spores.

An embodiment of the invention is for an additive which can be mixed into a batch aqueous system or through a continuous flow aqueous system. The additive can be in dry powder form or blended with an acceptable carrier to reduce the cost of the additive for a particular system.

The additive is contemplated to be added to the aqueous system in amount between about 0.01 wt % and 50 wt % based on the total weight of the aqueous system.

SALTS OF FORMIC ACID—The key ingredient is contemplated to be between about 30 wt % to about 50 wt % of a salt of a formic acid, and in the preferred embodiment, the salt is a potassium formate. While it is contemplated that a usable formulation to treat spore growth could contain between about 30 wt % and 50 wt % potassium formate, between about 0.1 wt % and 50 wt % potassium formate or a similar salt of formic acid such as cesium formate could be used.

In a second embodiment of the invention, a second salt of formic acid can be added to the first salt, wherein the first salt is potassium formate and the second salt is cesium formate. A preferred ratio of the potassium formate to the cesium formate would be 5:1.

A formulation of potassium formate with cesium formate would utilize between about 1 wt % and 50 wt % of the cesium formate, preferably between about 1 wt % and 5 wt % of the cesium formate when used in combination with another salt of formic acid, such as potassium formate.

The salts are preferably metal salts, such as cesium formate, sodium formate, zinc formate, lithium formate, calcium formate, potassium di-formate, potassium formate and combinations thereof.

KAVALACTONES—In yet another embodiment of the invention, an amount of active kavalactone can be added to the additive comprising the first salt of formic acid, notably the potassium formate. The additional kavalactone can be added in amounts between about 0.01 wt % and 50 wt % of the overall additive formulation. A preferred embodiment contemplates using between about 1 wt % to 50 wt % of kavalactone based on the wt % of the total composition prior to addition to the aqueous system. Yet another embodiment contemplates using between about 1 wt % to 20 wt % of active kavalactone based on the total wt % of the composition prior to introduction to the aqueous system.

Kavalactone is derived from piper methysticum or the Kava Kava plant of New Guinea, Indonesia area. The extract of the kava root is known to contain a class of structurally related chemical compounds, kavalactones. Kavalactones possess low bio-availability and are practically insoluble in water. The invention relates to the unexpected discovery that three kavalactones, diydrokawain, dihydromethysticin and kawain, exhibit inhibitory effect on the growth of fungi spores. Although is known that kavalactones have exhibited inhibitory effects on cytokines such as interleukin-12 (see U.S. Patent Application Publication No. 20020187169 filed May 11, 2002), which is hereby incorporated by reference. The reference does not teach any use attributed to it in combination with a salt of formic acid to inhibit spore growth after treatment of the vegetative state of the same fungi.

SURFACTANTS—Additionally, this composition may include surfactants. A sulfamic acid can be used as a stabilizer. The molar ratio of surfactant to the salt of formic acid is contemplated to range from 1:30 to 1:60.

It is contemplated that between about 0.5 wt % and 10.0 wt %, more preferably between 3 wt % and 5 wt %, surfactants could be used in this invention.

Other components that could be used in addition to or as substitution for the above noted surfactants include antioxidants, ultraviolet stabilizers, dyes, viscosifiers, and combinations of these.

A viscosifier usable in this invention would be xanthan gum, carboxymethyl cellulose, starch, guar gum, polyacrylates, polyacrylamides and combinations of these viscosifier.

CARRIERS—The formulation can be disposed in a carrier prior to introduction to an aqueous system.

The most preferred carrier is water. Different types of water can be used, including heavy water, distilled water, de-ionized water, tap water and combinations thereof.

Other than water, glycol can be used as a carrier, such as propylene glycol, butylene glycol, ethylene glycol and combinations of these.

An embodiment of the invention contemplates that the carrier can be a mixture of water, and glycol or a hydrocarbon.

Hydrocarbons which would be useful as carriers include mineral spirits, ethanol, butanol, propanol, naptha, and combinations thereof.

An embodiment of the invention contemplates that the fungi or mold growth controlling component can be spayed onto a surface, such as with a propellant. Typical propellants could be butane, propane, and inert gas such as nitrogen, carbon dioxide, air, and combinations of these.

If a propellant is used, it could comprise between 1% and 30% by volume of a desired container for spray on purposes.

Alternatively the formulation can be sponged on, brushed on, wiped on. Alternatively, components, such as wood or sheet rock could be soaked in the formulation or dredged in the formulation if a large vat full of the formulation was used.

AQUEOUS SYSTEM—The invention can be used with various aqueous systems such as paints, lubricants, transmission fluids, or air conditioning systems.

It is contemplated that the formulation can be used with cooling water towers, air cleaners, swimming pools, spas, industrial water systems, laundry detergents, bleaching agents, recycling water systems, oil field water, sweet water, gas scrubbers, or even water slides.

SURFACES—The formulation can be disposed on any number of surfaces to control spore growth.

ENCAPSULATION AGENT—Colloidal oatmeal can be used as an ingredient to form a paste with the novel composition and provide a means to encapsulate the spores to insure controlled growth.

A typical colloid oatmeal useable herein is oat gel, available from Quaker Oats.

A paste of the formulation could be created as follows (the powder is mixed at a shear rate):

a. 30 wt % of potassium formate;

b. 60 wt % of colloidal oatmeal; and c. 10 wt % tap water.

The unique oatmeal contains L-histines to kill the vegetative growth. The killing of the vegetative growth is an unexpected result of combining the oatmeal with the salt of the formic acid.

The ingredients are blended and mixed for about 2 minutes then the paste is ready to be applied to the surface.

An embodiment of the invention also contemplates that the carrier can be a mixture of water and glycol or a hydrocarbon.

The fungi growth to which the invention can be applied includes *Stachybotrys parvispora, Stachybotrys chartarum, Stachybotyrs kampalensis, Stachybotrys theobromae, Stachybotrys bisbyi, Stachybotrys cylindrospora, Stachybotrys dichroa, Stachybotrys oenanthes* or *Stachybotrys nilagerica* and combinations thereof.

An embodiment of the invention can also treat the fungi growth of *aspergillus fumigatus, aspergillus flavus, aspergillus oryzae, aspergillus niger, aspergillus foetidus, aspergillus phoenicus, aspergillus nomius, aspergillus ochraceus, aspergillus ostianus, aspergillus auricomus, aspergillus parasiticus, aspergillus sojae, aspergillus restrictus, aspergillus caesillus, aspergillus conicus, aspergillus sydowii, aspergillus tamari, aspergillus terreus, aspergillus ustus, aspergillus versicolor* and combinations thereof.

*Aspergillus terreus* can also be treated with the invention.

An embodiment of the invention can treat spores from the fungi growth of *absidia corymbifera, absidia coerulea, absidia glauca* and combinations thereof.

An embodiment of the invention can treat the fungi growth and spores of *cladosporium herbarum* and *fusarium oxysporum*.

An embodiment of the invention is contemplated to control spores from fungi growth of *acremonium strictum, alternaria* alternate, *apopphysomyces elegans*, Saksena *vasiformis* and combinations thereof.

The fungi growth of *Penicillium freii, Penicillium verrucosum, Penicillium hirsutum, Penicillium alberechii, Penicillum aurantiogriseum, Penicillium polonicum, Penicillium viridicatum, Penicillium brevicompactum, Penicillium chrysogenum, Penicillium griseofulvum, Penicillium glandicola, Penicillium coprophilum, Penicillium crustosum, Penicillium citrinum, Penicillium sartoryi, Penicillium westlingi, Penicillium corylophilum, Penicillium decumbens, Penicillium echinulatum, Penicillium solitum, Penicillium camembertii, Penicillium commune, Penicillium echinulatum, Penicillium sclerotigenum, Penicillium italicum, Penicillium expansum, Penicillium fellutanum, Penicillium charlesii, Penicillium janthinellum, Penicillium raperi, Penicillium madriti, Penicillium ochrochloron, Penicillium spinulosum, Penicillium glabrum, Penicillum thomii, Penicillium pupurescens,* and combinations thereof are also contemplated as susceptible to treatment with this invention.

In order that the invention described herein may be more readily understood, the following examples are set forth. It should be understood that these examples are for illustrative purposes only and not to be construed as limiting this invention in any manner. All references cited herein are expressly incorporated by reference in their entirety.

EXAMPLE 1

ADDITIVE—50 wt % of potassium formate is mixed with grout mix to add to a sealing composition, such as Easy Grout, in a ratio of 90:10 of sealing composition to additive.

EXAMPLE 2

ADDITIVE—50 wt % of potassium formate is mixed with 5 wt % of cesium formate and 45 wt % of a carrier. The carrier is water and is added to a coating for sheet rock in a ratio of 93:7 of sheet rock to additive coating known as Gypsum Brand available from US Gypsum, Inc.

EXAMPLE 3

ADDITIVE—30 wt % of potassium formate is mixed with an active kavalactone, namely Kava Kava Extract. The formed mixture is then added to a carrier, such as water, and added to a paint formulation such as a Sherman William Latex-based paint.

EXAMPLE 4

ADDITIVE—30 wt % of potassium formate is mixed with 2.5 wt % of cesium formate and 30 wt % of an active kavalactone, namely dihydrokawain forming a mixture. The mixture is then added to a carrier, namely, water in an amount up to 37.5 wt % of the water and added to a swimming pool water system.

The following is a chart of the results of treatment on various fungi:

| Example | Strachybotrys % killed | Penicillium % killed | Asperg % killed |
|---------|------------------------|----------------------|-----------------|
| 1 | 100 | 99.9+ | 100 |
| 2 | 100 | 100 | 100 |
| 3 | 100 | 100 | 100 |
| 4 | 100 | 100 | 100 |

The process of the invention can be used to control *Bacillus anthracis, Brucella abortus, Brucella melitensis, Brucella suis, Burkholderia mallei* (formally called *Pseudomonas mallei*), *Burkholderia pseudomallei* (formally called *Pseudomonas pseudomallei*), and *Botulinum* neurotoxin producing species of *Clostridium*.

While this invention has been described with emphasis on the preferred embodiments, it should be understood that within the scope of the appended claims the invention might be practiced or carried out in other ways than as specifically describe herein.

What is claimed is:

1. A building material adapted for controlling growth of vegetative fungi from spores comprising:
    a. a compressed calcium sulfate layer;
    b. a paper layer over the calcium sulfate layer;
    c. an adhesive for securing the papery layer to the calcium sulfate layer;
    d. the adhesive comprising from 30 wt % to 50 wt % of a salt of formic acid, wherein the salt of formic acid is potassium formate and a second salt of formic acid is added to the building material, disposed on the paper layer thereby forming drywall with an ionic lattice on the surface to prevent vegetative growth from fungi spores.

2. The building material of claim 1, wherein the second salt of formic acid is a metal salt.

3. The building material of claim 2, wherein the metal salt is cesium formate, sodium formate, zinc formate, lithium formate, calcium formate, potassium di-formate, potassium formate or combinations thereof.

4. The building material of claim 1, wherein the second salt of formic acid is an organic salt.

5. The building material of claim 4, wherein the organic salt, is ammonium formate, ethyl formate, methyl formate, amine formate, butyl formate, propyl formate or combinations thereof.

6. The building material of claim 1, further comprising an active kavalactone.

7. The building material of claim 6, wherein the active kavalactone is selected from the group consisting of a dihydrokawain, a dihydromethysticin, a kawain and combinations thereof.

8. The building material of claim 1, wherein the growth of vegetative fungi is *Stachybotrys parvisporai, Stachybotrys chartarum, Stachybotyrs kampalensis, Stachybotrys theobromae, Stachybotrys bisbyi, Stachybotrys cylindrospora, Stachybotrys dichroa, Stachybotrys oenanthes* or *Stachybotrys nilagerica* or combinations thereof.

9. The building material of claim 1, wherein the growth of vegetative fungi is *aspergillus fumigatus, aspergillus flavus, aspergillus oryzae, aspergillus niger, aspergillus foetidus, aspergillus phoenicus, aspergillus nomius, aspergillus ochraceus, aspergillus ostianus, aspergillus auricomus, aspergillus parasiticus, aspergillus sojae, aspergillus restrictus, aspergillus caesillus, aspergillus conicus, aspergillus sydowii, aspergillus tamari, aspergillus terreus, aspergillus ustus, aspergillus versicolor* or combinations thereof.

10. The building material of claim 1, wherein the growth of vegetative fungi is *absidia corymbifera, absidia coerulea, absidia glauca* or combinations thereof.

11. The building material of claim 1, wherein the growth of vegetative fungi is *acremonium strictum, alternaria* alternate, apopphysomyces *elegans*, saksena *vasiformis* or combinations thereof.

12. The building material of claim 1, wherein the growth of vegetative fungi is *penicillium freii, penicillium verrucosum, penicillium hirsutum, penicillium alberechii, penicillum aurantiogriseum, penicillium polonicum, penicillium viridicatum, penicillium brevicompactum, penicillium chrysogenum, penicillium griseofulvum, penicillium glandicola, penicillium coprophilum, penicillium crustosum, penicillium citrinum, penicillium sartoryi, penicillium westlingi, penicillium corylophilum, penicillium decumbens, penicillium echinulatum, penicillium solitum, penicillium camembertii, penicillium commune, penicillium echinulatum, penicillium sclerotigenum, penicillium italicum, penicillium expansum, penicillium fellutanum, penicillium charlesii, penicillium janthinellum, penicillium raperi, penicillium madriti, penicillium ochrochloron, penicillium spinulosum, penicillium glabrum, penicillum thomii, penicillium pupurescens*, or combinations thereof.

13. The building materials of claim 1, comprising a salt of citric acid, oxalic acid, maleic acid, acetic acid, fumaric acid, humic acid, fulvic acid, malic acid, glutaric acid, or glutamic acid.

14. A building material adapted for controlling growth of vegetative fungi from spores comprising:
a. a compressed calcium sulfate layer;
b. a paper layer over the calcium sulfate layer;
c. an adhesive for securing the papery layer to the calcium sulfate layer;
d. the adhesive comprising from 30 wt % to 50 wt % of a salt of formic acid, disposed on the paper layer thereby forming drywall with an ionic lattice on the surface to prevent vegetative growth from fungi spores;
wherein the building material is further comprising an active kavalactone;
wherein the salt of formic acid is potassium formate and a second salt of formic acid is added to the material.

15. The building material of claim 14 wherein the second salt of formic acid is a metal salt.

16. The building material of claim 15, wherein the metal salt is cesium formate, sodium formate, zinc formate, lithium formate, calcium formate, potassium di-formate, potassium formate or combinations thereof.

17. The building material of claim 14, wherein the second salt of formic acid is an organic salt.

18. The building material of claim 17, wherein the organic salt, is ammonium formate, ethyl formate, methyl formate, amine formate, butyl formate, propyl formate or combinations thereof.

19. The building material of claim 14, wherein the active kavalactone is selected from the group consisting of a dihydrokawain, a dihydromethysticin, a kawain and combinations thereof.

20. The building material of claim 14, wherein the growth of vegetative fungi is *Stachybotrys parvispora, Stachybotrys chartarum, Stachybotyrs kampalensis, Stachybotrys theobromae, Stachybotrys bisbyi, Stachybotrys cylindrospora, Stachybotrys dichroa, Stachybotrys oenanthes* or *Stachybotrys nilagerica* or combinations thereof.

21. The building material of claim 14, wherein the growth of vegetative fungi is *aspergillus fumigatus, aspergillus flavus, aspergillus oryzae, aspergillus niger, aspergillus foetidus, aspergillus phoenicus, aspergillus nomius, aspergillus ochraceus, aspergillus ostianus, aspergillus auricomus, aspergillus parasiticus, aspergillus sojae, aspergillus restrictus, aspergillus caesillus, aspergillus conicus, aspergillus sydowii, aspergillus tamari, aspergillus terreus, aspergillus ustus, aspergillus versicolor* or combinations thereof.

22. The building material of claim 14, wherein the growth of vegetative fungi is *absidia corymbifera, absidia coerulea, absidia glauca* or combinations thereof.

23. The building material of claim 14, wherein the growth of vegetative fungi is *acremonium strictum, alternaria* alternate, apopphysomyces *elegans*, saksena *vasiformis* or combinations thereof.

24. The building material of claim 14, wherein the growth of vegetative fungi is *penicillium freii, penicillium verrucosum, penicillium hirsutum, penicillium alberechii, penicillum aurantiogriseum, penicillium polonicum, penicillium viridicatum, penicillium brevicompactum, penicillium chrysogenum, penicillium griseofulvum, penicillium glandicola, penicillium coprophilum, penicillium crustosum, penicillium citrinum, penicillium sartoryi, penicillium westlingi, penicillium corylophilum, penicillium decumbens, penicillium echinulatum, penicillium solitum, penicillium camembertii, penicillium commune, penicillium echinulatum, penicillium sclerotigenum, penicillium italicum, penicillium expansum, penicillium fellutanum, penicillium charlesii, penicillium janthinellum, penicillium raperi, penicillium madriti, penicillium ochrochloron, penicillium spinulosum, penicillium glabrum, penicillum thomii, penicillium pupurescens*, or combinations thereof.

25. The building materials of claim 14, comprising a salt of citric acid, oxalic acid, maleic acid, acetic acid, fumaric acid, humic acid, fulvic acid, malic acid, glutaric acid, or glutamic acid.

26. A building material adapted for controlling growth of vegetative fungi from spores comprising:
a. a compressed calcium sulfate layer;
b. a paper layer over the calcium sulfate layer;

c. an adhesive for securing the papery layer to the calcium sulfate layer;
d. the adhesive comprising from 30 wt % to 50 wt % of a salt of formic acid, disposed on the paper layer thereby forming drywall with an ionic lattice on the surface to prevent vegetative growth from fungi spores;
wherein the building material is further comprising an active kavalactone and the active kavalactone is selected from the group consisting of a dihydrokawain, a dihydromethysticin, a kawain and combinations thereof;
wherein the salt of formic acid is potassium formate and a second salt of formic acid is added to the material.

27. The building material of claim 26 wherein the second salt of formic acid is a metal salt.

28. The building material of claim 27, wherein the metal salt is cesium formate, sodium formate, zinc formate, lithium formate, calcium formate, potassium di-formate, potassium formate or combinations thereof.

29. The building material of claim 26, wherein the second salt of formic acid is an organic salt.

30. The building material of claim 29, wherein the organic salt, is ammonium formate, ethyl formate, methyl formate, amine formate, butyl formate, propyl formate or combinations thereof.

31. The building material of claim 26, wherein the growth of vegetative fungi is *Stachybotrys parvispora, Stachybotrys chartarum, Stachybotyrs kampalensis, Stachybotrys theobromae, Stachybotrys bisbyi, Stachybotrys cylindrospora, Stachybotrys dichroa, Stachybotrys oenanthes* or *Stachybotrys nilagerica* or combinations thereof.

32. The building material of claim 26, wherein the growth of vegetative fungi is *aspergillus fumigatus, aspergillus flavus, aspergillus oryzae, aspergillus niger, aspergillus foetidus, aspergillus phoenicus, aspergillus nomius, aspergillus ochraceus, aspergillus ostianus, aspergillus auricomus, aspergillus parasiticus, aspergillus sojae, aspergillus restrictus, aspergillus caesillus, aspergillus conicus, aspergillus sydowii, aspergillus tamari, aspergillus terreus, aspergillus ustus, aspergillus versicolor* or combinations thereof.

33. The building material of claim 26, wherein the growth of vegetative fungi is *absidia corymbifera, absidia coerulea, absidia glauca* or combinations thereof.

34. The building material of claim 26, wherein the growth of vegetative fungi is *acremonium strictum, alternaria* alternate, *apopphysomyces elegans, saksena vasiformis* or combinations thereof.

35. The building material of claim 26, wherein the growth of vegetative fungi is *penicillium freii, penicillium verrucosum, penicillium hirsutum, penicillium alberechii, penicillum aurantiogriseum, penicillium polonicum, penicillium viridicatum, penicillium brevicompactum, penicillium chrysogenum, penicillium griseofulvum, penicillium glandicola, penicillium coprophilum, penicillium crustosum, penicillium citrinum, penicillium sartoryi, penicillium westlingi, penicillium corylophilum, penicillium decumbens, penicillium echinulatum, penicillium solitum, penicillium camembertii, penicillium commune, penicillium echinulatum, penicillium sclerotigenum, penicillium italicum, penicillium expansum, penicillium fellutanum, penicillium charlesii, penicillium janthinellum, penicillium raperi, penicillium madriti, penicillium ochrochloron, penicillium spinulosum, penicillium glabrum, penicillum thomii, penicillium pupurescens*, or combinations thereof.

36. The building materials of claim 26, comprising a salt of citric acid, oxalic acid, maleic acid, acetic acid, fumaric acid, humic acid, fulvic acid, malic acid, glutaric acid, or glutamic acid.

* * * * *